United States Patent
Atkin et al.

(10) Patent No.: US 7,530,809 B2
(45) Date of Patent: *May 12, 2009

(54) ULTRASONIC DENTAL HANDPIECE HAVING A ROTATABLE HEAD

(75) Inventors: Benjamin Atkin, Miami, FL (US); Haim Levy, Hod Hasharon (IL)

(73) Assignee: Discus Dental, LLC, Culver City, CA (US)

( * ) Notice: Subject to any disclaimer, the term of this patent is extended or adjusted under 35 U.S.C. 154(b) by 218 days.

This patent is subject to a terminal disclaimer.

(21) Appl. No.: 10/735,050

(22) Filed: Dec. 12, 2003

(65) Prior Publication Data
US 2004/0126737 A1 Jul. 1, 2004

Related U.S. Application Data

(60) Provisional application No. 60/524,903, filed on Nov. 26, 2003, provisional application No. 60/432,654, filed on Dec. 12, 2002.

(51) Int. Cl.
*A61C 3/03* (2006.01)
*A61C 3/08* (2006.01)

(52) U.S. Cl. .................................... 433/119

(58) Field of Classification Search ......... 433/118–124, 433/130; 16/DIG. 12
See application file for complete search history.

(56) References Cited

U.S. PATENT DOCUMENTS

| | | | |
|---|---|---|---|
| 3,518,766 A | 7/1970 | Burt | |
| 3,526,036 A | 9/1970 | Goof | |
| 3,526,219 A | 9/1970 | Balamuth | |
| 3,547,110 A | 12/1970 | Balamuth | |
| 3,636,947 A | 1/1972 | Balamuth | |
| 3,645,255 A | 2/1972 | Robinson | |
| 3,651,576 A | 3/1972 | Massa | |
| 3,654,502 A * | 4/1972 | Carmona et al. | 433/119 |
| 3,809,977 A | 5/1974 | Balamuth et al. | |
| 3,924,335 A | 12/1975 | Balamuth et al. | |
| RE28,752 E | 3/1976 | Balamuth et al. | |
| 4,169,984 A | 10/1979 | Parisi | |
| 4,176,454 A | 12/1979 | Hatter et al. | |
| 4,236,889 A | 12/1980 | Wright | |
| RE30,536 E | 3/1981 | Perdreaux, Jr. | |
| 4,260,380 A | 4/1981 | Nash | |
| 4,331,422 A | 5/1982 | Heyman | |
| 4,370,131 A | 1/1983 | Banko | |
| 4,484,893 A | 11/1984 | Finn | |
| 4,589,847 A | 5/1986 | Loge et al. | |
| 4,735,200 A | 4/1988 | Westerman | |
| 4,787,847 A | 11/1988 | Martin et al. | |
| 4,832,683 A | 5/1989 | Idemoto et al. | |
| 5,039,304 A | 8/1991 | Heil | |
| 5,286,192 A | 2/1994 | Dixon | |
| 5,395,240 A * | 3/1995 | Paschke et al. | 433/119 |

(Continued)

*Primary Examiner*—John J Wilson
(74) *Attorney, Agent, or Firm*—Christie, Parker & Hale, LLP

(57) ABSTRACT

An ultrasonic dental handpiece for holding a transducer is provided. The transducer converts electrical energy into ultrasonic vibrations. The dental handpiece includes a body, a rotator head, and a retainer ring. The body rotatably receives the transducer. The rotator head engages the transducer for rotation thereof. The retainer ring is fixedly coupled to one of the body and the rotator head and rotatably coupled to the other of the body and the rotator head, such that the rotator head is rotatably coupled to the body.

8 Claims, 5 Drawing Sheets

SECTION A-A

U.S. PATENT DOCUMENTS

| | | |
|---|---|---|
| 5,501,596 A | 3/1996 | Bailey |
| 5,531,597 A | 7/1996 | Foulkes et al. |
| 5,655,906 A * | 8/1997 | Coss et al. .................. 433/115 |
| 5,704,787 A | 1/1998 | Hickok et al. |
| 5,772,434 A | 6/1998 | Winston |
| 5,775,901 A | 7/1998 | Riso |
| 5,853,290 A | 12/1998 | Winston |
| 6,012,922 A | 1/2000 | Novak |
| 6,086,369 A | 7/2000 | Sharp et al. |
| 6,386,866 B1 | 5/2002 | Hecht et al. |
| 6,623,500 B1 * | 9/2003 | Cook et al. .................. 606/170 |
| 6,716,028 B2 * | 4/2004 | Rahman et al. ............. 433/119 |
| 2002/0040198 A1 | 4/2002 | Rahman et al. |
| 2002/0127512 A1 | 9/2002 | Chen et al. |
| 2003/0022129 A1 | 1/2003 | Rahman et al. |
| 2003/0073055 A1 | 4/2003 | Pollock et al. |
| 2003/0108844 A1 | 6/2003 | Rahman et al. |

* cited by examiner

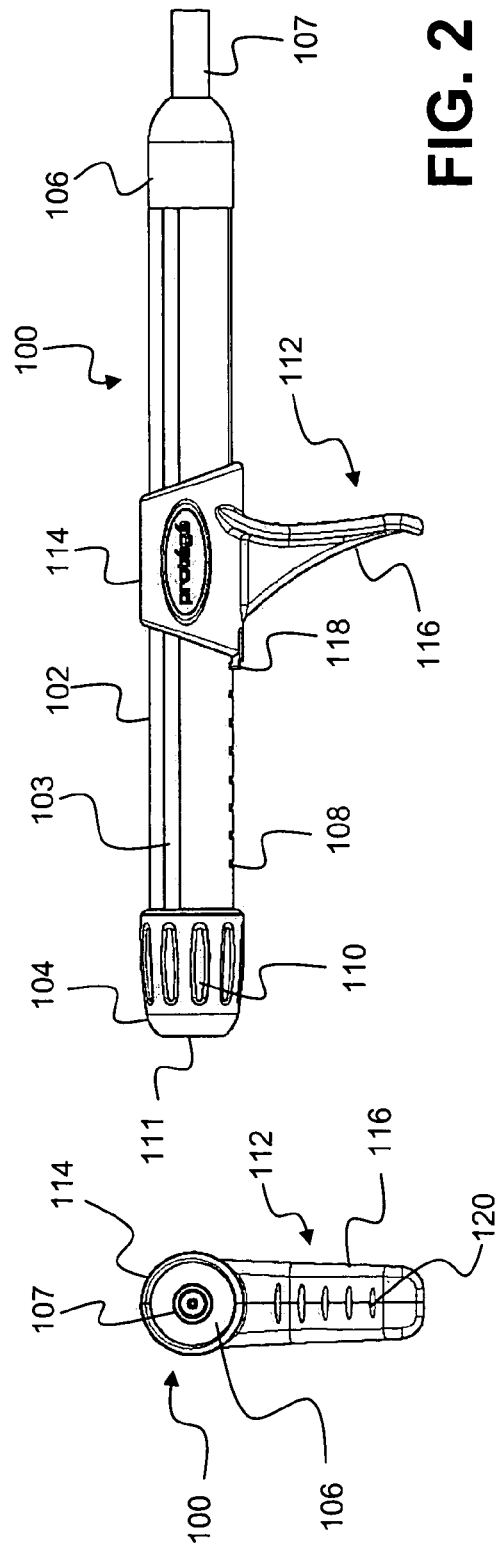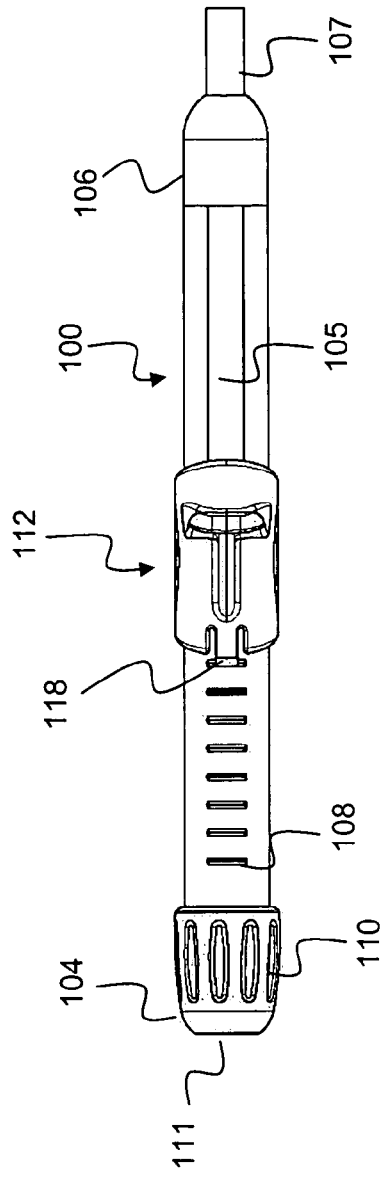

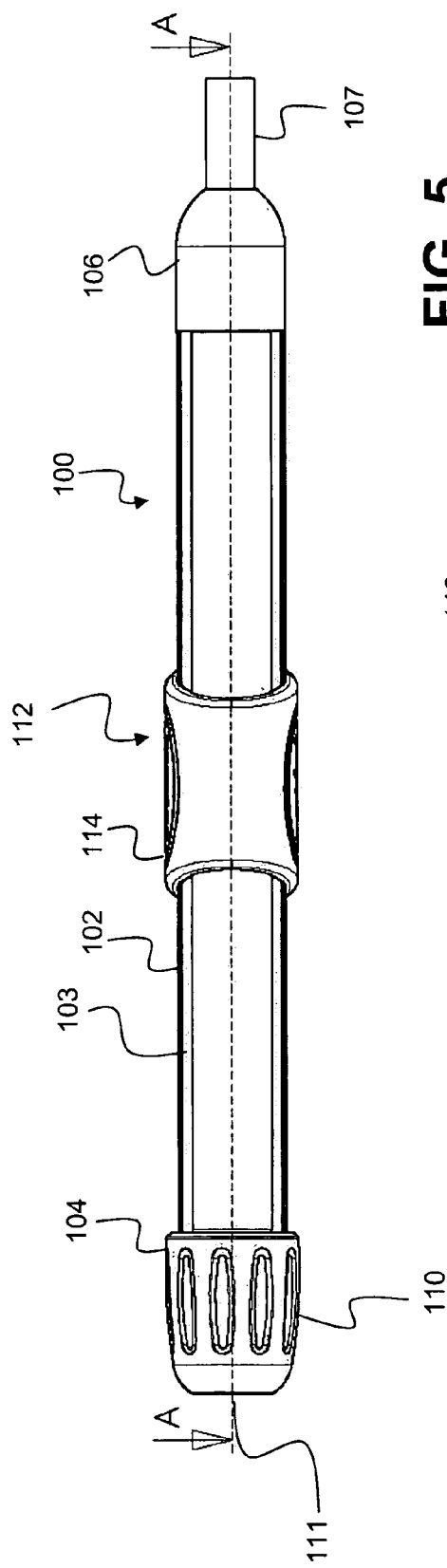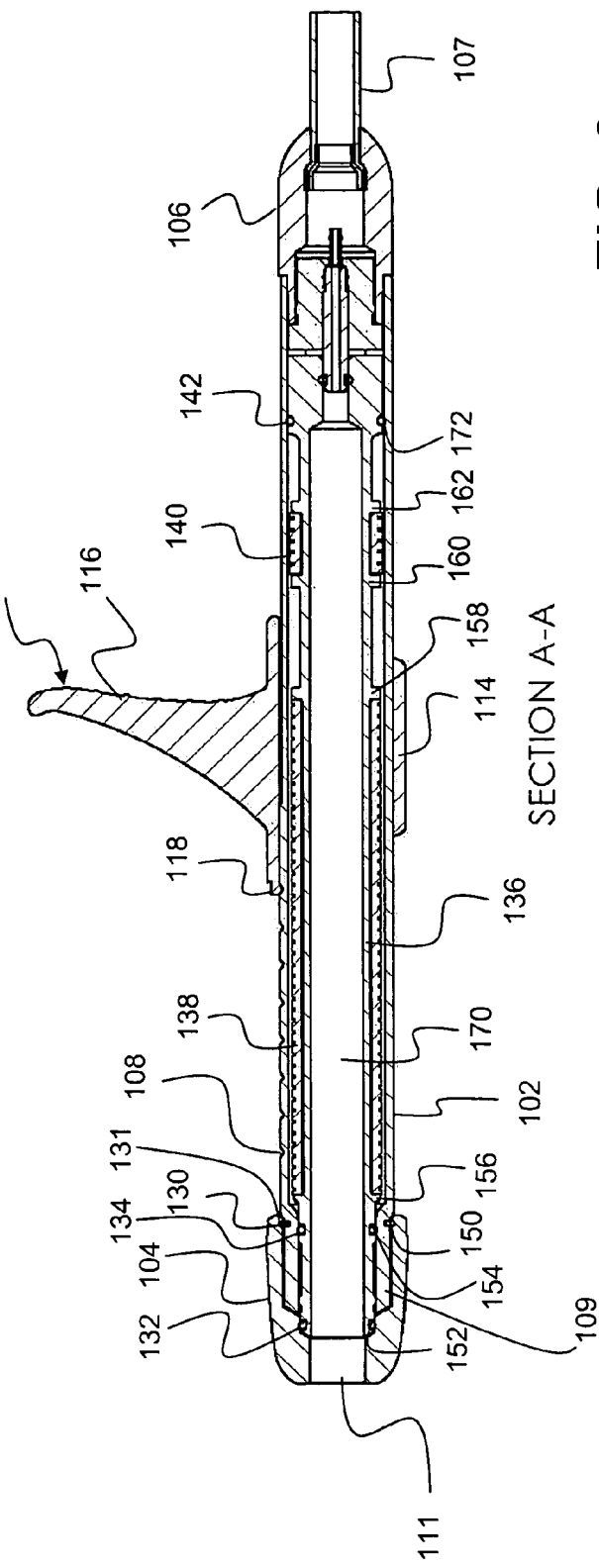

ULTRASONIC DENTAL HANDPIECE HAVING A ROTATABLE HEAD

CROSS-REFERENCE TO RELATED APPLICATIONS

This application claims the priority to and the benefit of U.S. Provisional Patent Application No. 60/432,654 entitled "Ultrasonic Dental Handpiece for Use with an Ultrasonic Dental Unit" filed Dec. 12, 2002, the entire content of which is incorporated herein by reference.

This application also claims the priority to and the benefit of U.S. Provisional Patent Application No. 60/524,903 entitled "Hand Grip for Dental Hygiene Tools" filed Nov. 26, 2003.

This application contains subject matter related to the subject matter disclosed in a commonly owned U.S. patent application Ser. No. 10/734,517 entitled "Ultrasonic Dental Insert Having a Hand Grip Fitted to a Retaining Ring," filed Dec. 12, 2003, the entire content of which is incorporated herein by reference.

FIELD OF THE INVENTION

The present invention is related to ultrasonic dental tools, and particularly to an ultrasonic dental handpiece having a rotatable head for receiving an insert.

BACKGROUND

Dental practitioners use ultrasonic dental tools (instruments) for dental treatments and procedures, such as scaling, periodontal treatments, root canal therapy, and the like. The ultrasonic dental tools typically include a handpiece coupled at one end (i.e., a proximal end) to an electrical energy and fluid source via a cable. The cable includes a hose to provide fluid (e.g., water) and conductors to provide electrical energy.

The other end (i.e., a distal end) of the handpiece has an opening intended to receive a replaceable insert with a transducer (e.g., magnetostrictive) carried on the insert. The transducer extends from a proximal end of the insert into a hollow interior of the handpiece. An ultrasonically vibrated tip extends from a distal end of the insert.

In using an ultrasonic dental tool during dental procedures, a dental practitioner typically re-orients the insert tip depending on which tooth is being treated. In making this angular adjustment, the practitioner typically takes the insert out of the patient's mouth, and rotates the insert to re-orient the tip at a desired angular position. Both hands are used for this rotation as the frictional forces that produce a tight fit of the insert in the handpiece must be overcome. During a typical treatment, the process of re-orienting the tip is carried out a number of times. This is not only time consuming, but also interrupts the ease and smooth flow of work.

In areas of the mouth where the practitioner chooses not to rotate the insert, the practitioner's wrist must be twisted sufficiently to achieve the same function. This twisting action is opposed by the resistance of the cable attached to the handpiece.

Therefore, there is a need for ultrasonic dental tools that are more comfortable and less fatiguing to use than conventional dental tools. Any such new improvements should be downwardly compatible with the numerous electrical energy and fluid sources, handpieces and inserts that are already present in dental offices.

SUMMARY

In an exemplary embodiment of the present invention, an ultrasonic dental handpiece for holding a transducer for converting electrical energy into ultrasonic vibrations is provided. The dental handpiece includes a body, a rotator head and a retainer ring. The body rotatably receives the transducer. The rotator head engages the transducer for rotation thereof. The retainer ring is fixedly coupled to one of the body and the rotator head and rotatably coupled to the other of the body and the rotator head, such that the rotator head is rotatably coupled to the body.

In another exemplary embodiment of the present invention, an ultrasonic dental unit including an insert and a handpiece is provided. The insert includes a tip and a transducer for converting electrical energy into ultrasonic vibrations. The handpiece includes a body, a rotator head, a retainer ring and a coil assembly. The body rotatably receives the insert. The rotator head engages the insert for rotation thereof. The retainer ring fixedly coupled to one of the body and the rotator head and rotatably coupled to the other of the body and the rotator head, such that the rotator head is rotatably coupled to the body. The coil assembly excites the transducer.

BRIEF DESCRIPTION OF THE DRAWINGS

These and other aspects of the invention may be understood by reference to the following detailed description, taken in conjunction with the accompanying drawings, wherein:

FIG. 2 is a side view of an ultrasonic dental handpiece in an exemplary embodiment of the present invention;

FIG. 3 is a bottom view of the ultrasonic dental handpiece of FIG. 2;

FIG. 4 is a rear view of the ultrasonic dental handpiece of FIG. 2;

FIG. 5 is an enlarged top view of the ultrasonic dental handpiece of FIG. 2;

FIG. 6 is a cross-sectional view of the ultrasonic dental handpiece of FIG. 5 taken along the line A-A;

DETAILED DESCRIPTION

In exemplary embodiments of the present invention, an ultrasonic dental handpiece has a rotator head, which rotates freely while the other parts of the handpiece, e.g., the body and the coils contained therein, remain stationary. This way, when an ultrasonic dental insert is inserted into the dental handpiece, it can be rotated together with the rotator head with relative ease.

Figure 1:
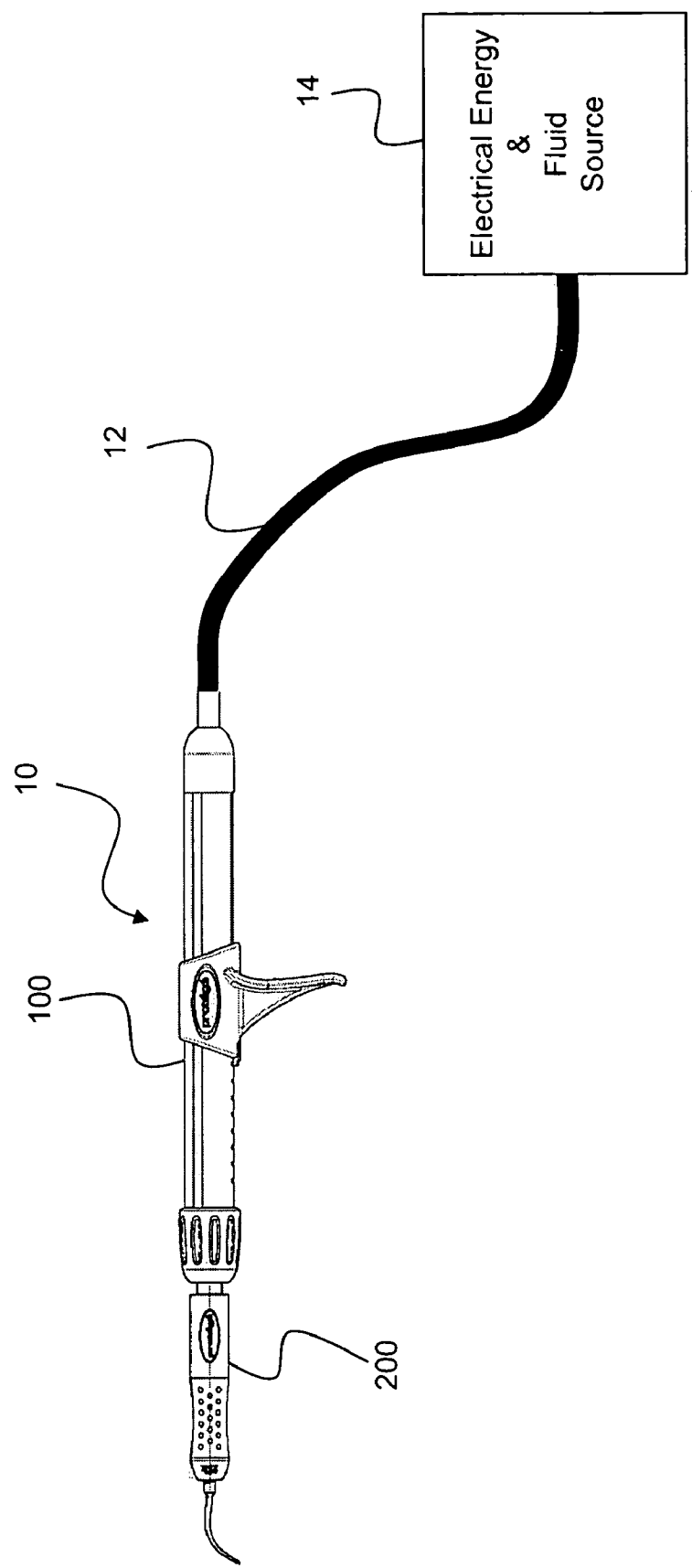
FIG. 1 is an ultrasonic dental unit (or system) including an ultrasonic dental tool attached to an electrical energy & fluid source.

FIG. 1 is an ultrasonic dental unit including an ultrasonic dental tool 10 attached to an electrical energy & fluid source 14 via a cable 12. The cable 12 includes a conduit for carrying fluid as well as wires for carrying electrical signals from the electrical energy & fluid source 14 to the ultrasonic dental tool 10. The ultrasonic dental tool 10 includes a handpiece 100 and an insert 200 received within the handpiece 100.

Referring now to FIGS. 2-5, the handpiece 100 includes a body 102, a rotator head 104 and an interconnect 106. The rotator head 104 located at a distal end of the handpiece 100 is rotatably coupled to the rest of the handpiece 100. The interconnect 106 located at a proximal end of the handpiece 100 is coupled to a cable (e.g., the cable 12 of FIG. 1) for providing electrical signals as well as fluid (e.g., water) to the handpiece 100. The interconnect 106 has a strain reliever 107 formed thereon to relieve strain between the interconnect 106 and the cable.

Since the body 102 is fixedly coupled to the interconnect 106, which in turn is fixedly attached to the cable, the handpiece 100 cannot be rotated easily. Therefore, by allowing the rotator head 104 to rotate with respect to the rest of the handpiece 100, a dental practitioner does not have to repeatedly re-orient the entire dental tool to treat different teeth and/or different areas of a tooth. Further, since the rotator head 104 of the handpiece 100 can be rotated rather easily with respect to the body 102, a dental practitioner does not have to take the insert out of the patient's mouth and rotate the insert using both hands to re-orient the tip of the insert at a desired angular position. Therefore, time associated with re-orienting the tip a number of times during the dental treatment is reduced, and the flow of work is not interrupted as much, thereby resulting in a smooth work flow and a reduction of time.

The rotator head 104 has a generally cylindrical shape, a hollow interior, and an opening at each end of the interior, which is used to receive the distal end of the body 102 at one end and a dental insert at the other end. For example, at its distal end, the rotator head 104 has formed thereon an opening 111 for receiving an insert.

The rotator head 104 has formed around its outer peripheral surface a plurality of indentations 110. Each indentation 110 has an elongated elliptical (or rectangular) shape with its major axis in the direction parallel to the central axis of the handpiece 100. The indentations 110 facilitate grasping of the rotator head 104 by a dental practitioner to rotate it, for example, with respect to the body 102 (e.g., using only one hand). In other embodiments, the rotator head 104 may have a number of protrusions formed thereon instead of the indentations.

The body 102 has formed thereon a pair of grooves 103 that are equidistant from the top and traverse substantially the whole length of the body 102. The grooves 103 are used to mount a hand grip 112 on the handpiece 100. The body 102 has also formed thereon at its bottom near the distal end of the body 102 a plurality of substantially evenly spaced slots 108 that are used to keep the hand grip 112 from moving in the direction of the axis of the handpiece 100. The body 102 has also formed thereon at its bottom near the proximal end a groove 105 that is co-linear to the slots 108. The groove 105 engages the hand grip 112 together with the grooves 103 to keep the hand grip 112 from rotating about the central axis of the handpiece 100. The grooves may not be used in other embodiments.

The hand grip 112 has an engagement portion 114, which has a generally cylindrical shape and a hollow interior. The engagement portion 114 is slipped onto the body 102 similar to a sleeve, and engages the body 102 such that the engagement portion envelopes a portion of the body 102. The engagement portion has formed thereon a resilient cantilever portion 118, which is used to engage one of the slots 108 on the body 102. The engagement portion 114 has attached to its bottom surface a handle 116, which is used by a dental practitioner to hold the handpiece 100 during dental procedures. The handle also facilitates rotating of the rotator head 104 using one hand. The handle 116 has formed on its back surface a plurality of indentations or protrusions 120, which are used to facilitate grasping by a dental practitioner.

Figure 7:
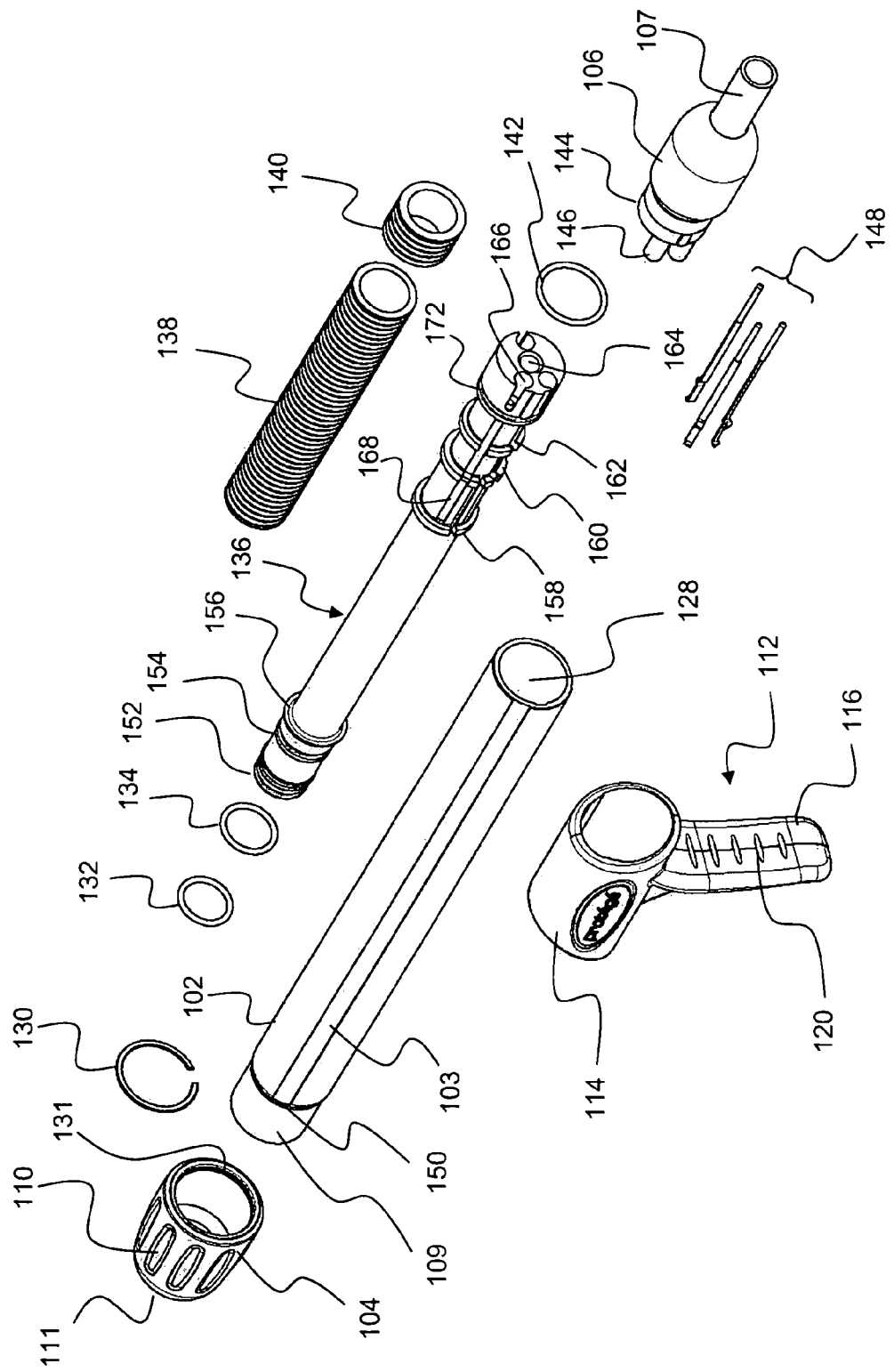
FIG. 7 is an enlarged exploded view of the ultrasonic dental handpiece of FIG. 2.

Referring now to FIGS. 6 and 7, the handpiece 100 further includes a retainer ring 130, which is made of metal, such as stainless steel. The retainer ring 130 is substantially circular in shape, but does not quite form a complete circle. The retainer ring 130 is flexible (resilient) and works as a spring in that the ends that are not connected together can be brought closer together by applying pressure, but they separate when the pressure is removed.

The rotator head 104 has formed on the inner surface near its proximal end a circular groove 131 that are used to engage the retainer ring 130. The retainer ring 130 is installed in the circular groove 131, for example, by applying pressure on the retainer ring 130 to compress it, and releasing it once the retainer ring 130 has been aligned with the groove 131. Upon installation, the retainer ring 130 is locked to and is fixed with respect to the rotator head 104.

After locking the retainer ring 130 to the groove 131, the rotator head 104 is coupled with the body 102 by receiving the distal end of the body 102 into the rotator head opening at its proximal end. The body 102 has formed at its distal end an engagement portion 109, which has a radius that is smaller than the radius of the rest of the body 102. At a joint between the engagement portion 109 and the rest of the body 102 is formed a circular groove 150 on an outer surface of the engagement portion 109. When the engagement portion 109 is inserted into the rotator head 104, the retainer ring rotatably engages the groove 150 such that the rotator head 104 is rotatably coupled to the body 102. In other embodiments, the rotating ring may be fixedly coupled to the body 102 and rotatably coupled to the rotator head 104.

The body 102 has an inner surface, which defines a hollow cavity 128 formed therethrough, into which a bobbin 136 is received. During a typical ultrasonic dental tool operation, fluid is pumped through the cable and the handpiece 100 to the tip of the insert. The vibrating tip of the insert breaks the fluid stream into a spray. The spray not only keeps the tip cool, but also keeps the surface of the tooth cool and provides protection against tissue damage. The fluid path through the handpiece 100 (through the bobbin 136) needs to be sealed such that no leakage occurs until the fluid stream exits from the insert at the distal end through a fluid delivery channel.

The bobbin 136 has a generally cylindrical shape, and formed near its distal end a pair of circumferential grooves 152 and 154. The grooves 152 and 154 engage O-rings 132 and 134, respectively, and are used to prevent fluid from leaking out of the handpiece 100. For example, the O-ring 132 forms a water tight seal with the inner surface of the rotator head 104, while the O-ring 134 forms a water tight seal with the inner surface of the engagement portion 109.

The bobbin 136 has also formed thereon a pair of circular flanges 156 and 158. A long coil 138 is mounted on the bobbin 136 between the flanges 156 and 158. The bobbin 136 has also formed thereon a pair of circular flanges 160 and 162 near its proximal end. A short coil 140 is mounted on the bobbin between the circular flanges 160 and 162. The coils, for example, are made from insulated wires. In other embodiments, the coils may have substantially the same length, or the longer coil may be mounted near the proximal end of the bobbin 136.

Near its proximal end, the bobbin 136 has formed thereon a circular groove 172 for seating an O-ring 142. By seating the O-ring 142 in the groove 172, a water tight seal is formed between the bobbin 136 and the inner surface of the body 102 such that the fluid does not leak from the handpiece 102.

The bobbin 136 has an inner surface, which defines a generally cylindrical cavity 170 for transmitting fluid from the proximal end to the distal end, and has an opening 164 at its proximal end for receiving fluid into the cylindrical cavity 170. The bobbin 136 has also formed at its proximal end a plurality (e.g., three) of openings 166, which are used to receive plug pins 148 in the bobbin 136. The plug pins 148 are made of electrically conductive material such as copper. The bobbin 136, the body 102, the rotator head 104, the hand grip 112 and the casing for the interconnect 106 are made of a suitable synthetic polymeric material, such as that commonly referred to as "plastic" (e.g., high temperature resin). For example, they may be fabricated using ULTEM®, which is an amorphous thermoplastic polyetherimide available from GE Plastics.

The bobbin 136 has also formed thereon a plurality of linear grooves 168 that are aligned with and extend from the respective openings 166 to the coils 138 and/or 140. The pins 148 installed, respectively, in the openings 166 and the grooves 168 are soldered and/or otherwise electrically connected to the coils 138 and/or 140, and are used to transmit electrical signals from the electrical energy & fluid source via the cable through the interconnect 106.

The interconnect 106 has also formed thereon a plurality (e.g., three) of elongated sockets 146 that engage the openings 166, respectively. The elongated sockets 146, for example, are formed on a connector portion 144 of the interconnect 106. The elongated sockets 146 have formed therein electrical contacts for making electrical connections with the plug pins 148, respectively. The electrical contacts are electrically connected at the other end with the wires in the cable, for example, to supply electrical energy to the coils 138 and 140, thereby energizing them.

Figure 8:
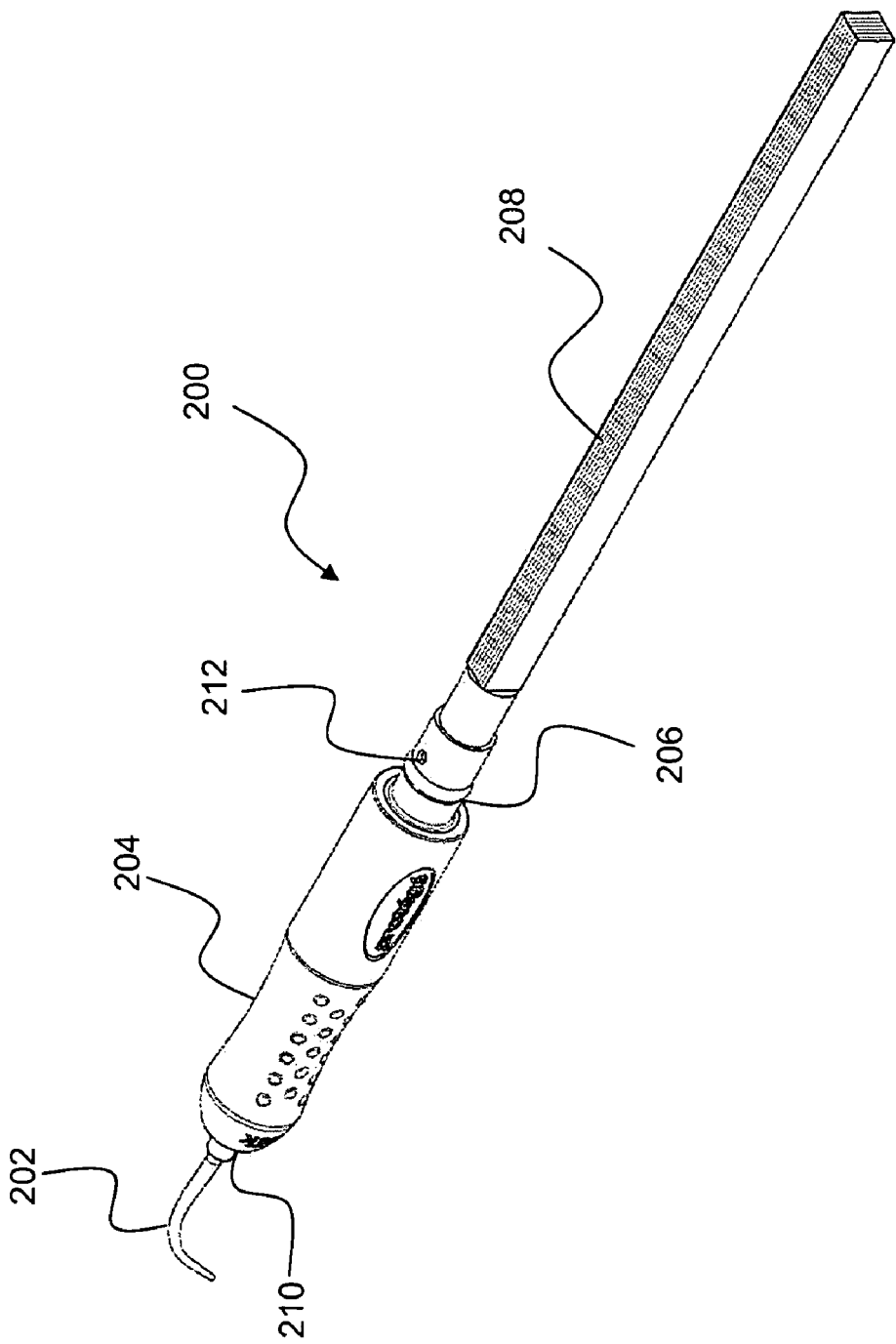
FIG. 8 is a perspective view of an insert that can be received in the ultrasonic dental handpiece of FIG. 2.

FIG. 8 illustrates a ultrasonic dental insert 200 that can be received in the dental handpiece 100 in exemplary embodiments of the present invention. The insert 200 is received through the opening 111 into the cavity 170 of the bobbin 136. For example, the dental insert includes a tip 202 at its distal end and a transducer 208 at its proximal end. The dental insert further comprises a connecting body disposed between and attached to the tip and the transducer. The dental insert includes a hand grip 204, which may be made of high temperature resin. The rest of the insert, other than the transducer, is made of stainless steel, for example.

The transducer 208, for example, may be formed from a stack of thin nickel plates (e.g., 16 laminated nickel alloy strips, which are 90% nickel manganese (NiMn)) that are arranged in parallel. The nickel plates may be joined together at both ends at a braze joint using a braze compound including cadmium free silver solder and high temperature brazing flux.

The insert 200 is a magnetostrictive type, in which the nickel plates 208 can convert the electrical energy into ultrasonic vibrations when the coils 138 and 140 are energized using the electrical signals from the cable. The insert 200 has an O-ring 206 mounted thereon for engaging and pressure fitting the inner surface of the rotator head 104 such as to form a water tight seal and also such that the insert (and therefore its tip) is rotated together with the rotator head 104 with respect to the body 102. Any other suitable dental inserts available to those skilled in the art may be used instead of the dental insert 200.

The insert 200 has a hole 212 formed thereon for receiving fluid from the cylindrical cavity 170 of the bobbin 136. The grip 204 has at its distal end near the tip 202 a passageway 210 for the fluid to exit from the insert. In other embodiments, the insert may have an opening at the end of its tip, a groove formed on the tip, or an external tube for enabling the fluid to exit the insert.

During an operation, the stack of thin nickel plates 208 vibrate at a frequency equal to the stack's natural frequency with excitation induced by the coils. After placing the insert in the handpiece and the electrical energy source is powered on, the operator manually tunes the frequency of the electrical energy source until it reaches the resonance frequency, i.e., the natural frequency of the insert. Alternatively, auto-tune units may automatically lock on the insert resonance frequency once powered on. At this time, the stack begins vibrating. This vibration of the stack is amplified and transmitted to the tip 202. Ultrasonic inserts used in the United States are typically designed to vibrate at 25 kHz or 30 kHz frequencies.

It will be appreciated by those of ordinary skill in the art that the present invention can be embodied in other specific forms without departing from the spirit or essential character hereof. The present description is therefore considered in all respects to be illustrative and not restrictive. The scope of the present invention is indicated by the appended claims, and all changes that come within the meaning and range of equivalents thereof are intended to be embraced therein.

For example, while the handpiece of the present invention is described in reference to a magnetostrictive type of ultrasonic dental tools commonly used in the United States, the principles of the present invention can equally as well be applied to piezoelectric type of ultrasonic dental tools that are commonly used in Europe.

We claim:

1. An ultrasonic dental unit comprising:
   an insert comprising a tip and a transducer for converting electrical energy into ultrasonic vibrations; and
   a handpiece comprising:
      a body rotatably receiving the insert;
      a rotator head engaging the insert for rotation thereof, wherein the rotator head envelopes at least a portion of the body, such that the rotator head is adapted to be directly engaged by a user such that the insert is rotated with respect to the body by applying a force directly to the rotator head;
      a retainer ring fixedly coupled to one of the body and the rotator head and rotatably coupled to the other of the body and the rotator head, such that the rotator head is rotatably coupled to the body; and
      a coil assembly for exciting the transducer.

2. The ultrasonic dental unit of claim 1, further comprising an electrical energy & fluid source for supplying electrical signals and fluid to the handpiece.

3. The ultrasonic dental unit of claim 1, wherein the retainer ring is a metallic spring that can be compressed for installation within the rotator head.

4. The ultrasonic dental unit of claim 1, wherein the coil assembly comprises a bobbin and at least one coil mounted on the bobbin.

5. The ultrasonic dental unit of claim 1, wherein the transducer comprises a stack of thin nickel plates.

6. The ultrasonic dental unit of claim 5, wherein the stack of thin nickel plates generate the ultrasonic vibrations when the coil assembly is energized.

7. The ultrasonic dental unit of claim 1, wherein the insert further comprises a connecting body disposed between and attached to the tip and the transducer.

8. The ultrasonic dental handpiece of claim 1, wherein the transducer comprises a magnetostrictive type or a piezoelectric type.

* * * * *